(12) United States Patent
Markart

(10) Patent No.: US 6,315,951 B1
(45) Date of Patent: Nov. 13, 2001

(54) TEST STRIP MEASURING SYSTEM

(75) Inventor: Ernst Markart, Munich (DE)

(73) Assignee: LRE Technology Partner GmbH, Munich (DE)

(*) Notice: Subject to any disclaimer, the term of this patent is extended or adjusted under 35 U.S.C. 154(b) by 0 days.

(21) Appl. No.: 09/315,276

(22) Filed: May 20, 1999

(30) Foreign Application Priority Data

May 20, 1998 (DE) .......................................... 298 09 191 U

(51) Int. Cl.$^7$ ................................................ G01N 33/48
(52) U.S. Cl. ............................ 422/61; 422/58; 422/68.1; 422/82.01; 422/82.02; 422/82.05; 422/82.06; 422/83; 422/98; 436/149; 436/150
(58) Field of Search ............................ 422/58, 61, 68.1, 422/82.01, 82.02, 83, 98, 99, 82.05, 82.06; 436/149, 150, 178

(56) References Cited

U.S. PATENT DOCUMENTS

| | | | |
|---|---|---|---|
| 5,281,395 | * | 1/1994 | Markart et al. ................... 422/82.05 |
| 5,504,011 | * | 4/1996 | Gavin et al. ........................... 436/69 |
| 5,786,584 | * | 7/1998 | Button et al. ......................... 235/462 |
| 5,945,341 | * | 8/1999 | Howard, III ............................ 436/46 |
| 5,989,917 | * | 11/1999 | McAleer et al. ....................... 436/46 |
| 6,036,092 | * | 3/2000 | Lappe .............................. 235/462.13 |

* cited by examiner

*Primary Examiner*—Jill Warden
*Assistant Examiner*—Dwayne K Handy
(74) *Attorney, Agent, or Firm*—McCormick, Paulding & Huber LLP

(57) ABSTRACT

In a test strip measuring system including a test strip with at least one test field and a measuring device for measuring optically or by means of electrical currents detectable values of the test field, a code carrier is provided for insertion into the measuring device along with the test strip. The code carrier, by way of an electronic memory, stores information used by the measuring device in measuring the test field of the test strip. The code carrier also includes a data processing device for reading the stored information from the memory and for supplying it to the measuring device. The selection of the program for reading the stored information from its memory and other factors are so controlled by controlled information supplied from the measuring device as to make it extremely difficult for copiers to make usable copies of the code carrier by merely copying the information stored in the code carrier memory.

7 Claims, 1 Drawing Sheet

TEST STRIP MEASURING SYSTEM

FIELD OF THE INVENTION

The invention concerns a measuring system including a test strip having at least one test field and a measuring device for optically or by way of electric currents measuring the test field, with a code carrier being associated with the test strip or with a test strip package containing at least one test strip, which code carrier carries coded information about the manufacturing date of the test strip or about the measurement to be carried out.

BACKGROUND OF THE INVENTION

Measuring systems of the above mentioned kind are used for example for monitoring the concentration of certain substances in body fluids, for example for blood sugar determination. Test strips of different manufacturing batches can have calibration data which deviates from one test strip to another. Therefore, this calibration data must be communicated to the measuring device before the carrying out of the measurement. It is also possible that one such measuring device is suited to the carrying out of different measurements. If so the measuring device must be informed before the insertion of the test strip, for which particular measurement the inserted test strip is intended. This data is generally stored in the code carrier. There exists non-authorized suppliers, who attempt to deliver test strips by themselves for systems of the previously mentioned kind. Since the calibration data of given test strips do not differ grossly from batch to batch, these suppliers may try to copy the code carrier, including the coded information, even if they can not read the coded information. In view of this the measuring accuracy of the measuring systems suffers with corresponding danger for patients who use such a measuring system.

The invention has as its object to hinder the copying of the code carriers with their own coded information, or to see to it that such duplicated code carriers are unuseful.

SUMMARY OF THE INVENTION

The above object is solved for a measuring system of the above mentioned kind in that the code carrier has an electronic memory for storing the coded information and a data processing device for reading and transmitting the stored data to the measuring device, whereby the data processing device is controllable from the measuring device by means of variable control information. By means of this variable control information the data processing device can be caused, for example, to select one of several programs for reading and/or changing the stored data. For instance by means of the control information the data processor can be informed in which sequence a data word or data sentence is to be read, whether the data is to be ignored, inverted, connected with one another according to a pregiven rule, displaced by a given bit position count, or the like. It is also imaginable, that by means of the control information the starting address of the data to be read is identified. Which control information is transmitted, that is which program is chosen in the data processing device, can be fixed in the measuring device, or determined by way of a contingency procedure has been selected.

According to a further feature of the invention, the above mentioned object is solved in a measuring system of the previously mentioned kind in that the test strip carries a physically detectable value, that the measuring device has a sensor for detecting this value, and that the coded information is given by the magnitude of the physically detectable value. For example an ohmic resistance can be applied to the test strip the magnitude of which is measurable by the measuring device, with a resistance magnitude also being coded on the code carrier. The measuring device compares the measured resistance magnitude with the coded magnitude. If the two magnitudes do not agree, within a given tolerance, the test strip is rejected by the measuring device. The resistance magnitude can be so applied to the code carrier that it is a difficult for a copier to determine where and in what form the resistance has been applied to the code carrier. In a preferred embodiment of the invention the code carrier can have a characteristic contour, which is formed complementary to the shape of a code carrier receiver of the measuring device. Then, by way of a key/lock principal only a given code carrier can be inserted into the measuring device.

This principal can also be further expanded in that contact elements are provided on the code carrier which are intended to contact with countercontact elements in a code carrier receiver of the measuring device, with the contact elements and the counter-contact elements being arranged relative to one another in a kind of key/lock complementary relationship.

BRIEF DESCRIPTION OF THE DRAWINGS

The following description explains the invention in combination with the accompanying drawings by way of exemplary embodiments. The drawings are.

DETAILED DESCRIPTION OF THE PREFERRED EMBODIMENTS

Figure 1:
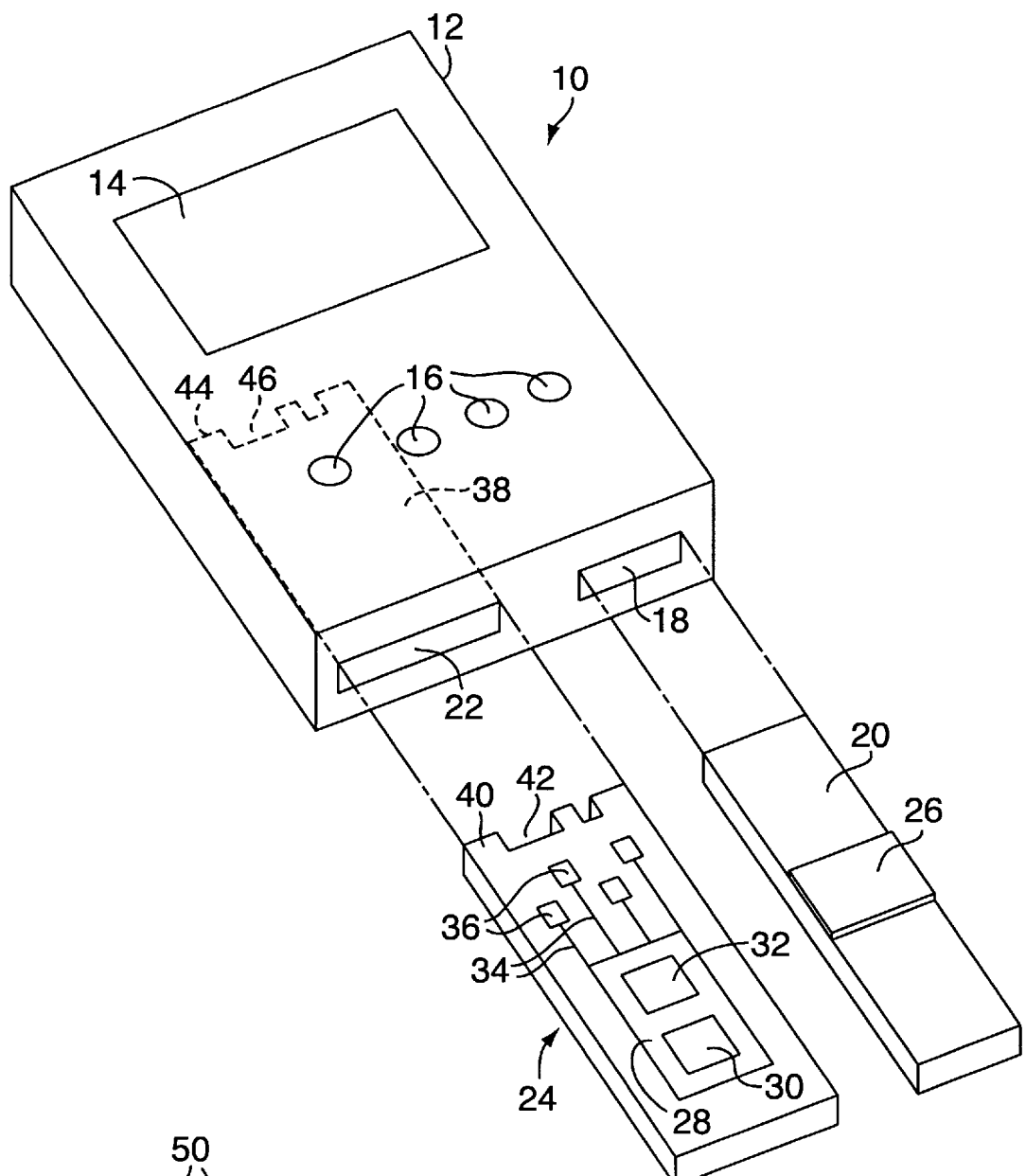
FIG. 1—a schematic illustration of a measuring system in accordance with the invention with a measuring device and test strip or code carrier.

In FIG. 1 is seen a measuring device, indicated generally at 10, with a housing 12, an indicator device 14 and operating elements 16. The housing 12 has an insertion opening 18 for a test strip 20 as well as a further insertion opening 22 for a code carrier 24.

The test strip 20 has a test field 26 onto which a fluid to be investigated is to be dropped. The measuring device 10 contains a measuring mechanism for optically or by way of electrical currents measuring the test field 26 in order, by way of the measured data, to determine for example the concentration of a given substance in the dropped on liquid. Such a measuring device and test strip are known and therefore do not need to be described in further detail.

The code carrier 24 contains an electronic assembly 28 containing at least a memory 30 and a data processing device 32. The assembly 28 can be unified into an integrated module. The assembly 28 is connected by conductors 34 with contact elements 36 which are associated with non-illustrated counter-contact elements in a code carrier receiver 38, shown by broken lines, in the measuring device 10. The memory 30 serves to store data which, for example, concerns information about the type of measurement to be carried out, the characteristic curve of the test strip, or manufacturing data of the test strip. The data processing device 32 contains different programs with the help of which the data contained in the memory 30 in coded form is read out in different ways and can be transmitted to the measuring device 10. Which of these programs is activated is determined by control information transmitted from the measuring device 10. This control information can be selected in a previously established way or also according to a contingency principal. The control information thereby determines whether the data transmitted to the measuring device is to be ignored, or not ignored, inverted, stored, or shifted by given bit positions, on a given logical combination, forwardly or rearwardly, or in some other way read out of the memory. Also by way of the control information the starting address of the read out data can be supplied. It is therefore not sufficient for a potential copier to only read out and copy the coded information from the memory 30. This information by itself is worthless, so long as it is not known in what way the information is to be read. The measuring device itself can read this information only with the help of the data processing device 32, whose internal reading program however can be so secret that it, if at all, can be ascertained only with extreme difficulty.

One sees further in FIG. 1 that the contact elements 36 are arranged in a pregiven pattern which also corresponds to a corresponding arrangement of the counter-contact elements in the measuring device 10. Further, the forward edge of the code carrier 24 facing the measuring device 10 is provided with projections 40 and recesses 42. These projections and recesses correspond to complementary recesses 44 and projections 46 in the code carrier receiver 38. The projections and recesses 40, 42 interdigitate with the recesses 44 and the projections 46 according to the key/lock principal. In the same way the contact elements 36 cooperate with the corresponding counter-contact elements in the measuring device 10. Thereby it is assured that only the correct code carrier 24 can be so inserted into the measuring device 10 that a communication is possible between the code carrier and the measuring device.

Figure 2:
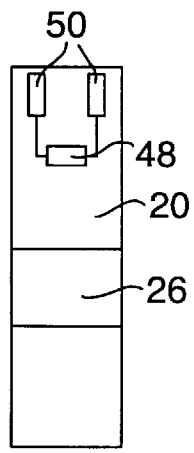
FIG. 2—a modified embodiment of a test strip.

FIG. 2 shows a modified test strip 20 on which an ohmic resistance 48 is arranged whose ends are connected with the contact elements 50. Through these contact elements 50 the resistance 48 can be measured by a suitable measuring mechanism in the measuring device 10. A magnitude of resistance can be applied to the code carrier in some outwardly nonvisible way. This can be achieved in the form of data or also by way of a physically measurable value. In the code carrier receiver 38 of the measuring device 10 a corresponding reading or sensing arrangement must be provided. The measured resistance magnitude of the test strip is compared with the resistance magnitude contained on the code carrier. If these two magnitudes do not agree with one another within a given tolerance, the measuring device can not measure the test strip.

As used in the following claims, the term "information about the test strip" is meant, without limitation, to include information giving the date of test strip manufacture, the characteristic curve of the test strip, and/or information as to the type of measurement to be carried out with the test strip.

What is claimed is:
1. A measuring system comprising:
a test strip (20) having at least one test field (26),
a measuring device (10) for optically or by way of electrical currents measuring the test field (26), and
a code carrier (24) separate from the test strip and replaceably insertable into and removable from the measuring device,
the code carrier carrying an electronic memory (30) for storing coded information about the test strip,
the code carrier also carrying a data processing device (32) for reading and transmitting the coded information stored by the electronic memory to the measuring device (10), and
the data processing device (32) being controllable from the measuring device (10) by variable control information supplied to the data processing device (32) by the measuring device (10).

2. A measuring system according to claim 1, wherein: the data processing device (32) in dependence on the control information selects one program from a number of programs contained in the data processing device for dealing with the coded information stored in the electronic memory (30).

3. A measuring system according to claim 1, wherein:
a starting address of the stored coded information to be read out of the electronic memory (30) is selectable in dependence on the control information.

4. A measuring system according to claim 1, wherein:
at least a part of the coded information carried by the code carrier is the magnitude of a physically detectable value, and
the measuring device (10) has a sensor for detecting the magnitude of the physically detectable value.

5. A measuring system according to claim 4, wherein:
the physically detectable value is an outwardly non-visible ohmic resistance of a pregiven magnitude arranged on the code carrier.

6. A measuring system according to claim 1, wherein:
the code carrier (24) has a shape with a characteristic contour (40, 42) which is complementary to a shape of a code carrier receiver (38) of the measuring device (10).

7. A measuring system according to claim 1, wherein:
contact elements (36) are provided on the code carrier (24), which contact elements are intended to come into contact with counter-contact elements in a code carrier receiver (38) of the measuring device (10),
the contact elements (36) and the counter-contact elements are arranged complementary to one another whereby the all of the contact elements (36) of an inserted code carrier (24) make contact with all of their respective counter-contact elements of the receiver (38) only if the contact elements (36) of the inserted code carrier are arranged complementary to the counter-contact elements of the receiver (38).

* * * * *